United States Patent
Kierce et al.

(10) Patent No.: US 8,931,636 B2
(45) Date of Patent: Jan. 13, 2015

(54) BLADE EXCHANGE DEVICE, SYSTEM AND METHOD

(75) Inventors: Paul C. Kierce, Cohasset, MA (US); Kenneth V Freeman, Laconia, NH (US)

(73) Assignee: ATC Technologies, Inc., Wilmington, MA (US)

( * ) Notice: Subject to any disclaimer, the term of this patent is extended or adjusted under 35 U.S.C. 154(b) by 443 days.

(21) Appl. No.: 13/052,344

(22) Filed: Mar. 21, 2011

(65) Prior Publication Data

US 2011/0226645 A1 Sep. 22, 2011

Related U.S. Application Data (60) Provisional application No. 61/315,883, filed on Mar. 19, 2010.

(51) Int. Cl.
*B65D 85/68* (2006.01)
*A61B 19/02* (2006.01)
*A61B 17/3215* (2006.01)
*A61B 17/3217* (2006.01)
*A61B 17/3209* (2006.01)
*A61B 17/322* (2006.01)
*A61B 17/00* (2006.01)

(52) U.S. Cl.
CPC ......... *A61B 19/0256* (2013.01); *A61B 17/3215* (2013.01); *A61B 17/3217* (2013.01); *A61B 17/32093* (2013.01); *A61B 17/322* (2013.01); *A61B 2017/00747* (2013.01); *A61B 2017/00876* (2013.01)
USPC .............................. 206/355; 206/352; 30/339

(58) Field of Classification Search
CPC ................... A61B 17/322; A61B 2017/00747; A61B 2017/00576
USPC ............ 206/349, 352, 354–360; 30/40.2, 339
See application file for complete search history.

(56) References Cited

U.S. PATENT DOCUMENTS

| | | | | |
|---|---|---|---|---|
| 1,849,251 | A | * | 3/1932 | Sherman ........................ 206/356 |
| 2,305,600 | A | * | 12/1942 | Benjamin ...................... 206/356 |
| 2,344,962 | A | * | 3/1944 | Benjamin ...................... 206/356 |
| 5,528,811 | A | * | 6/1996 | Abidin et al. ................. 206/352 |
| 5,662,221 | A | * | 9/1997 | Abidin et al. ................. 206/354 |
| 2009/0259241 | A1 | * | 10/2009 | Nakamura ..................... 206/363 |

* cited by examiner

*Primary Examiner* — Mickey Yu
*Assistant Examiner* — Chun Cheung
(74) *Attorney, Agent, or Firm* — Grossman Tucker Perreault & Pfleger, PLLC

(57) ABSTRACT

A blade exchange device may be used to remove or install a blade on a medical or surgical instrument such as a dermatome. The blade exchange device generally includes a base portion and a blade engaging portion that engages the blade being removed or installed. The blade exchange device may be used in a system that also includes a magnetic tool for coupling and moving the blades that are removed or installed. The blade exchange device, system and method may be used, for example, with commercially available dermatome instruments such as the type known as the Goulian-Weck knife.

8 Claims, 11 Drawing Sheets

BLADE EXCHANGE DEVICE, SYSTEM AND METHOD

CROSS-REFERENCE TO RELATED APPLICATIONS

The present application claims the benefit of U.S. Provisional Patent Application Ser. No. 61/315,883 filed on Mar. 19, 2010, which is fully incorporated herein by reference.

TECHNICAL FIELD

The present invention relates to removing and installing blades on surgical or medical instruments.

BACKGROUND INFORMATION

Surgical or medical instruments often use sharp razor blades. One such instrument is known as a dermatome and is used to produce thin slices of skin from a donor area in order to make skin grafts, for example, to reconstitute skin areas damaged by burns or other trauma. A conventional dermatome generally includes a handle that securely holds the blade and allows manipulation of the blade during use. One example of a dermatome is known as a Goulian-Weck knife. In this type of a dermatome, the handle removably secures the blade by friction and a guard is located over the blade to guard the blade edge and allow a certain thickness of tissue to be removed.

A surgeon may use several blades during a procedure such as a skin graft procedure. Removing and installing blades presents significant hazards to health care workers performing or assisting with such procedures. With Goulian-Weck knives, for example, the health care worker often must grasp or handle the blade directly in an effort to remove the blade from the handle or to install a new blade on the handle. Because the blade is securely held on the instrument, removing and installing blades may be difficult and the health care worker may be seriously cut by the exposed blade.

BRIEF DESCRIPTION OF THE DRAWINGS

These and other features and advantages will be better understood by reading the following detailed description, taken together with the drawings wherein.

DETAILED DESCRIPTION

A blade exchange device may be used to remove and/or install a blade on a medical or surgical instrument such as a dermatome. The blade exchange device generally includes a base portion and a blade engaging portion that engages the blade being removed or installed. The blade exchange device may be used in a system that also includes a magnetic tool for coupling and moving the blades that are removed or installed. The blade exchange device, system and method may be used, for example, with commercially available dermatome instruments such as the type known as the Goulian-Weck knife.

Referring to FIGS. 1A-1D, one embodiment of a blade exchange device 100 includes a base portion 110 and a blade engaging portion 120 extending from the base portion 110 to engage a blade 102. In this embodiment, the blade engaging portion 120 extends from one end of the base portion 110. The blade engaging portion 120 includes one or more blade locating protrusions, such as pins 122, configured to engage one or more holes 104 and/or notches 106 in the blade 102. In one example, a plurality of pins 122 may form a pattern corresponding to the holes 104 and/or notches 106 that are die cut or stamped in the blade 102 during manufacturing. The pins 122 allow the blade 102 to be properly aligned and kept stable during removal or installation. Although four pins are shown, other numbers of pins or types of locating protrusions may also be used.

The blade engaging portion 120 may also include a handle receiving region 124 configured to receive the handle (not shown) of the instrument when the locating protrusion(s) 122 engages the hole(s) 104 and/or notch(es) 106 in the blade 102. The handle receiving region 124 may generally be in the form of a channel that extends below a top surface of the blade engaging portion 120 adjacent the locating protrusion(s) 122. The handle receiving region 124 may include a sloped or angled surface 125, for example, with an angle in a range of about 20° to 30° relative to a horizontal plane and specifically about 23°. The angled surface 125 guides the blade securing end of the handle to the blade 102 on the blade engaging portion 120 such that the blade securing end is aligned with the blade 102 to facilitate blade installation.

The blade engaging portion 120 may also include a blade guard receiving portion or well 126 for use in removing and installing blade guards over the blade on the handle. The blade guard receiving portion 126 is generally sized and configured to receive and secure the blade guard in an upright position. The blade guard receiving portion 126 may include a blade guard engaging portion 127 that engages the blade guard to prevent movement of the blade guard in at least one direction during installation and removal. The blade guard engaging portion 127 may formed by, for example, a portion having a narrower dimension that prevents the blade guard from being removed from the blade guard receiving portion 126 when a force is applied in a generally horizontal direction. The blade guard receiving portion 126 may also be configured with a stop to prevent the blade from going too far forward and thus provide alignment of the blade and guard. The blade guard receiving portion 126 may further include an angled surface 128 to facilitate alignment of the handle as mentioned above.

In one example embodiment, the base portion 11 has a length of about 6 in. and a width of about 3 in., the handle receiving portion 124 has a depth of about 0.13 in., and the blade guard receiving portion 126 has a width of about 0.25 in. and a depth of about 0.335 in.

Figure 1A:
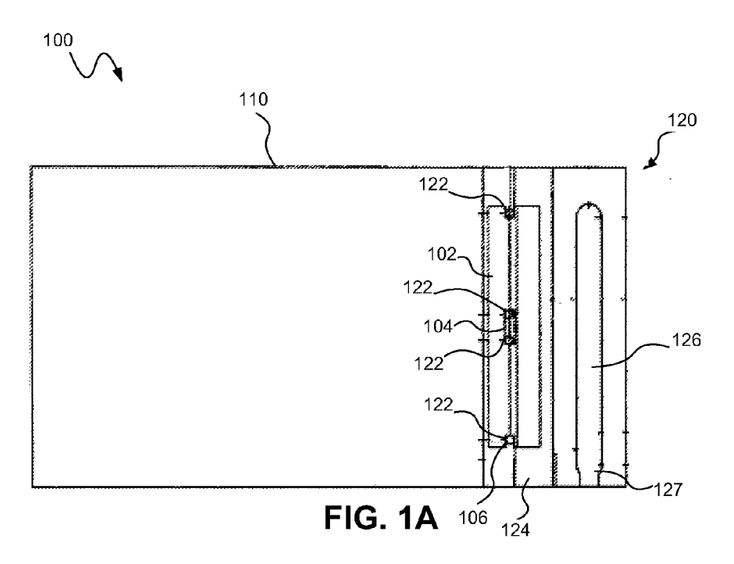
FIG. 1A is a plan view of a blade exchange device, consistent with one embodiment.
Figure 1B:
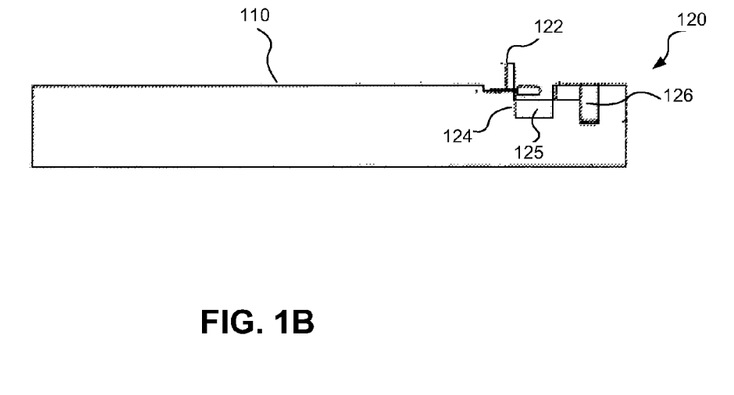
FIG. 1B is a side view of the blade exchange device shown in FIG. 1A.
Figure 1C:
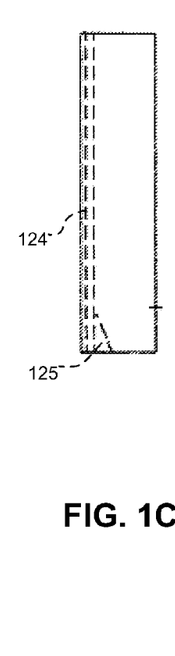
FIG. 1C is an end view of the blade exchange device shown in FIG. 1A illustrating a handle receiving region.
Figure 1D:
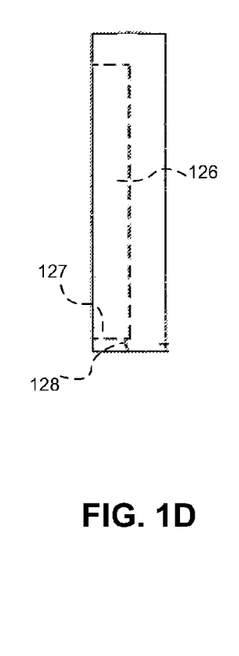
FIG. 1D is an end view of the blade exchange device shown in FIG. 1A illustrating a blade guard receiving region.
Figure 2A:
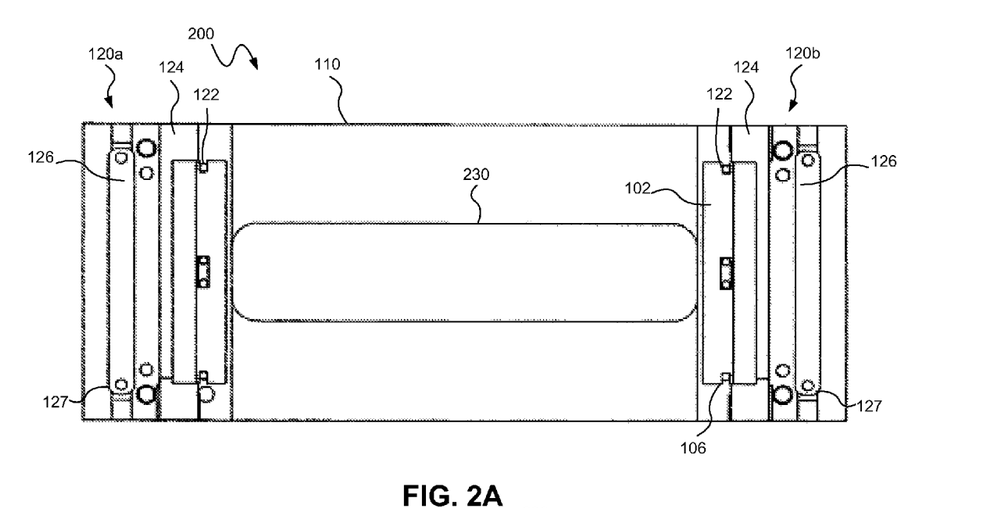
FIG. 2A is a plan view of a blade exchange device, consistent with another embodiment.
Figure 2B:
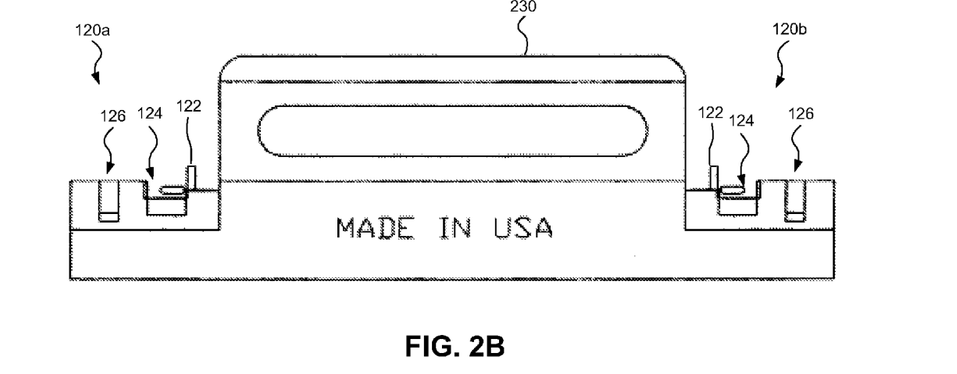
FIG. 2B is a side view of the blade exchange device shown in FIG. 2A.

FIGS. 2A-2B show another embodiment of a blade exchange device 200. The blade exchange device 200, consistent with this embodiment, includes blade engaging portions 120a, 120b extending from each end of the base portion 110. The blade engaging portions 120a, 120b may be mirrored or essentially the same on each side. This configuration facilitates left and right hand use. The blade exchange device 200 further includes a handle 230 extending from the base portion 110 to facilitate grasping of the blade exchange device 200 by the user.

Figure 3A:
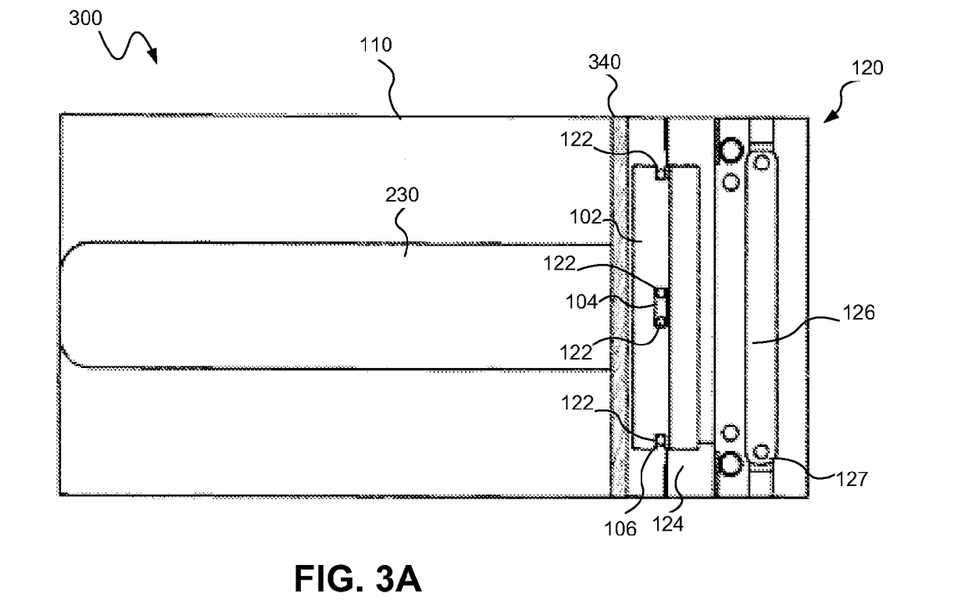
FIG. 3A is a plan view of a blade exchange device, consistent with a further embodiment.
Figure 3B:
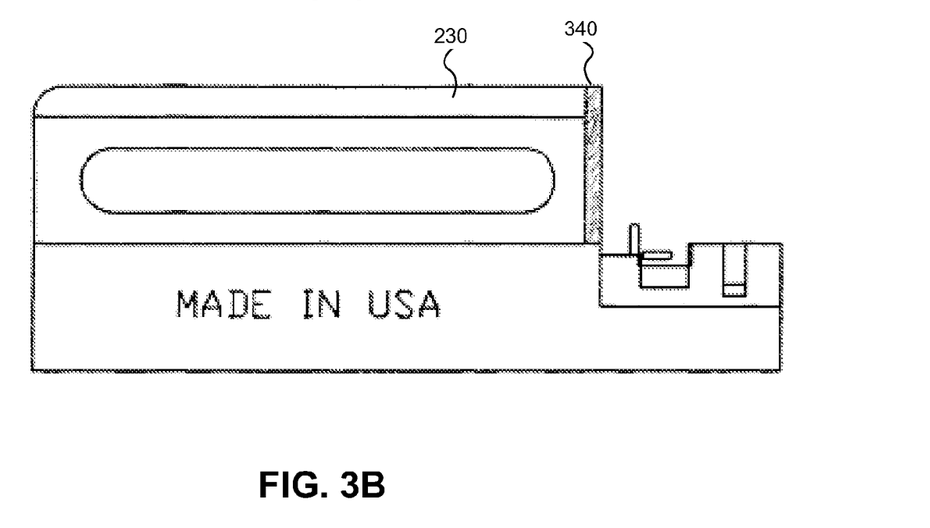
FIG. 3B is a side view of the blade exchange device shown in FIG. 3A.

FIGS. 3A-3B show a further embodiment of a blade exchange device 300. The blade exchange device 300, consistent with this embodiment, includes a shield 340 between the base portion 110 and the blade engaging portion 120. The shield 340 may include, for example, a plate extending from the base portion 110 adjacent the handle 230. The shield 340 may protect the hand of the user grasping the base portion 110 or handle 230 when removing or installing the blade.

Figure 4A:
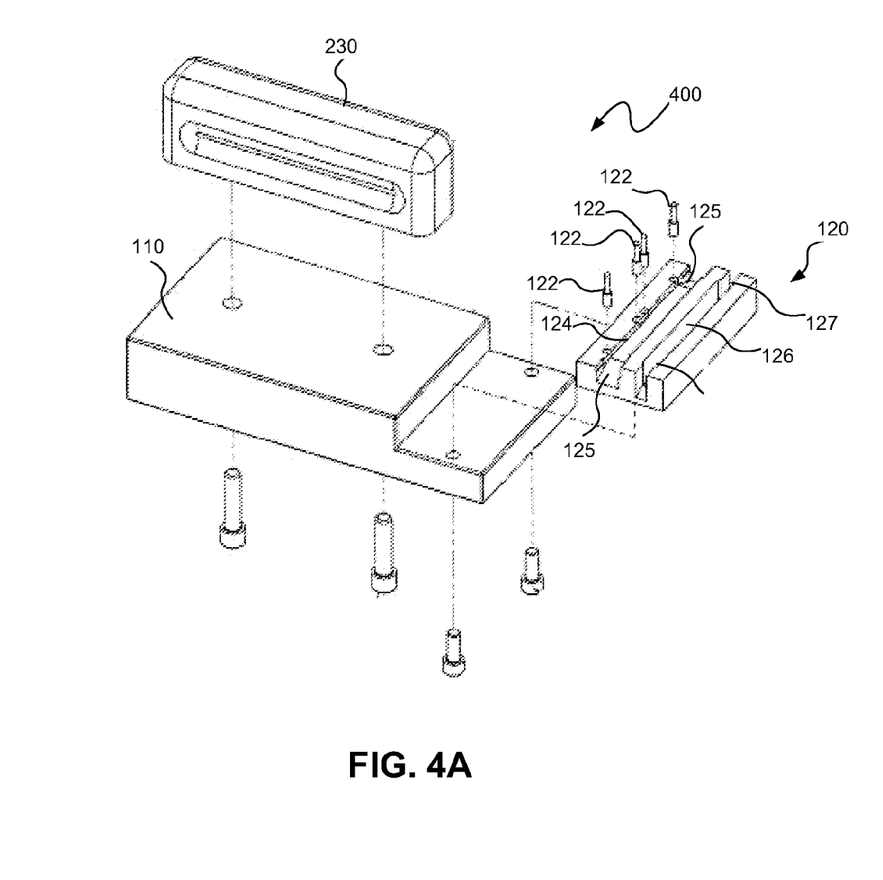
FIG. 4A is an exploded view of a blade exchange device, consistent with yet another embodiment.
Figure 4B:
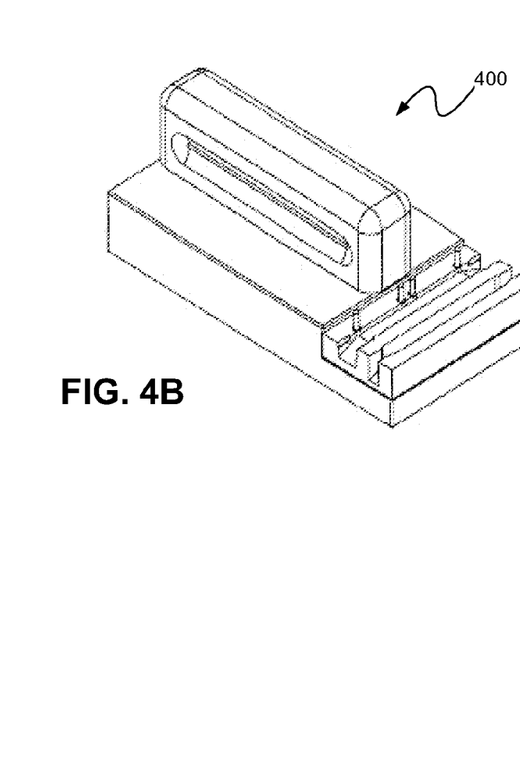
FIG. 4B is a perspective view of the blade exchange device shown in FIG. 4A.

FIGS. 4A-4B show yet another embodiment of a blade exchange device 400. The blade exchange device 400, consistent with this embodiment, includes a single blade engaging portion 120 that facilitates use with either the left hand or right hand. The single blade engaging portion 120 may include a handle receiving region 124 and blade guard receiving region 126 extending from one side to an opposite side such that the handle and blade guard may be received from either side. As illustrated in this embodiment, the blade exchange device 400 may also include a handle 230 and blade exchanging portion 120 that are attached to the base portion 110, for example, using screws, bolts, or other threaded members.

The blade exchange device, consistent with the embodiments described above, may have a weight sufficient to counter the opposing forces that are applied when removing or installing a blade. The weight of the blade exchange device may be, for example, in the range of about 16.0 oz to 80.0 oz (or about 1-5 lbs.) and more particularly may be about 38 oz to 50 oz. Embodiments of the blade exchange device may be made of a material capable of providing the desired weight, such as stainless steel, aluminum or other metallic materials. The bottom surface of the blade exchange device may be substantially flat to maximize surface area contact and friction to prevent slipping when in use. In other embodiments, an anti-slip material, such as a rubber pad, may be attached to the bottom of the blade exchange device to prevent the device from slipping during use.

Figure 5:
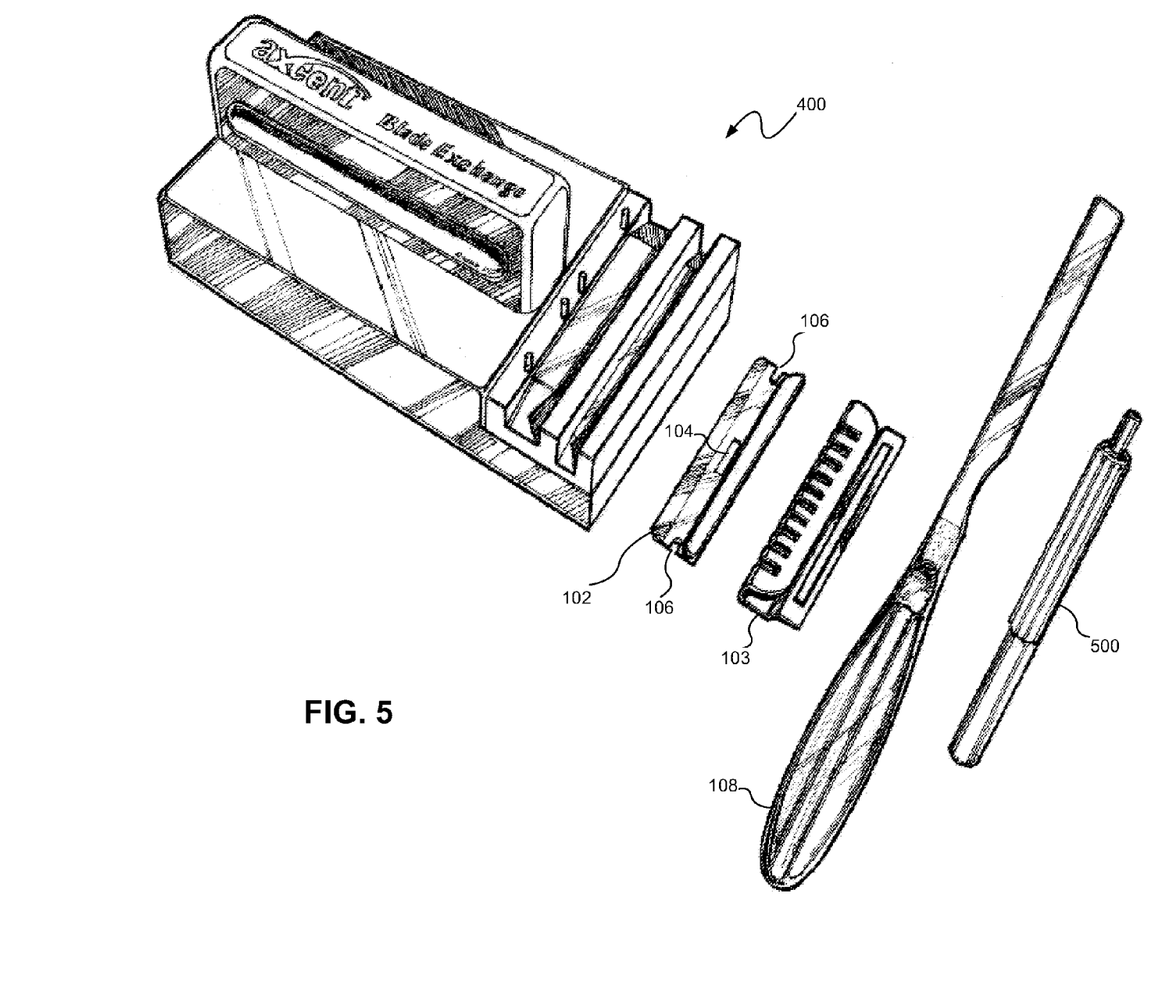
FIG. 5 is a perspective view of a blade exchange system, consistent with one embodiment.
Figure 6:
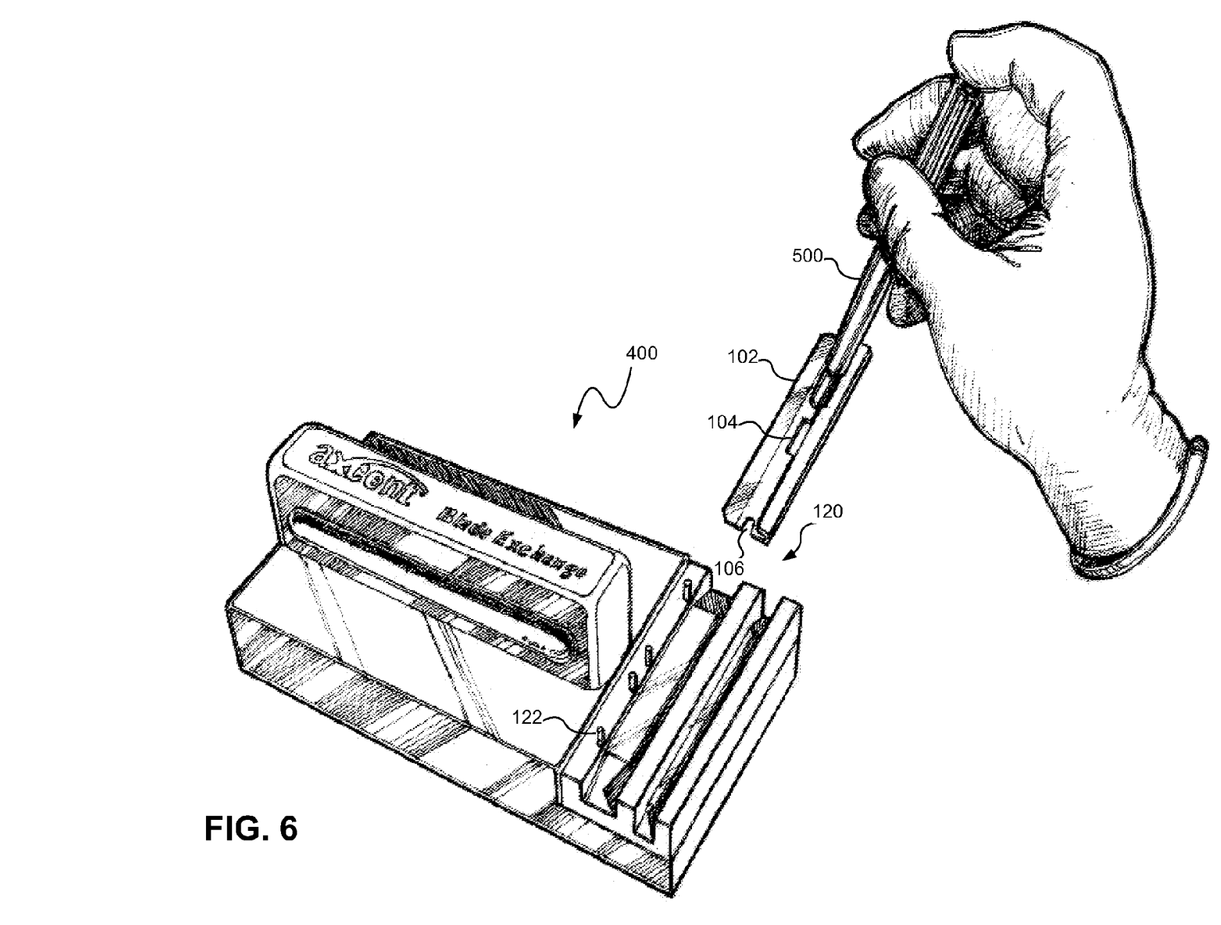
FIGS. 6-11 are perspective views of the blade exchange system shown in FIG. 5 and illustrating the installation of a blade and blade guard.

FIG. 5 illustrates a blade exchange device 400, consistent with the embodiment shown in FIG. 4, together with a blade 102, a guard 103, and a handle 108. In yet another embodiment, a blade exchange system may include a magnetic tool 500 together with the blade exchange device 400. The magnetic tool 500 is configured to magnetically attract and couple the blade 102 to lift the blade for positioning on the blade engaging portion 120 (e.g., during blade installation) or extraction from the blade engaging portion 120 (e.g., during blade removal). The magnetic tool 500 may include an on/off magnetic device capable of selectively magnetically coupling the blade 102. In yet a further embodiment, the magnetic tool 500 may be provided together with replacement blades 102 in kit form, for example, in sterile packaging.

Figure 7:
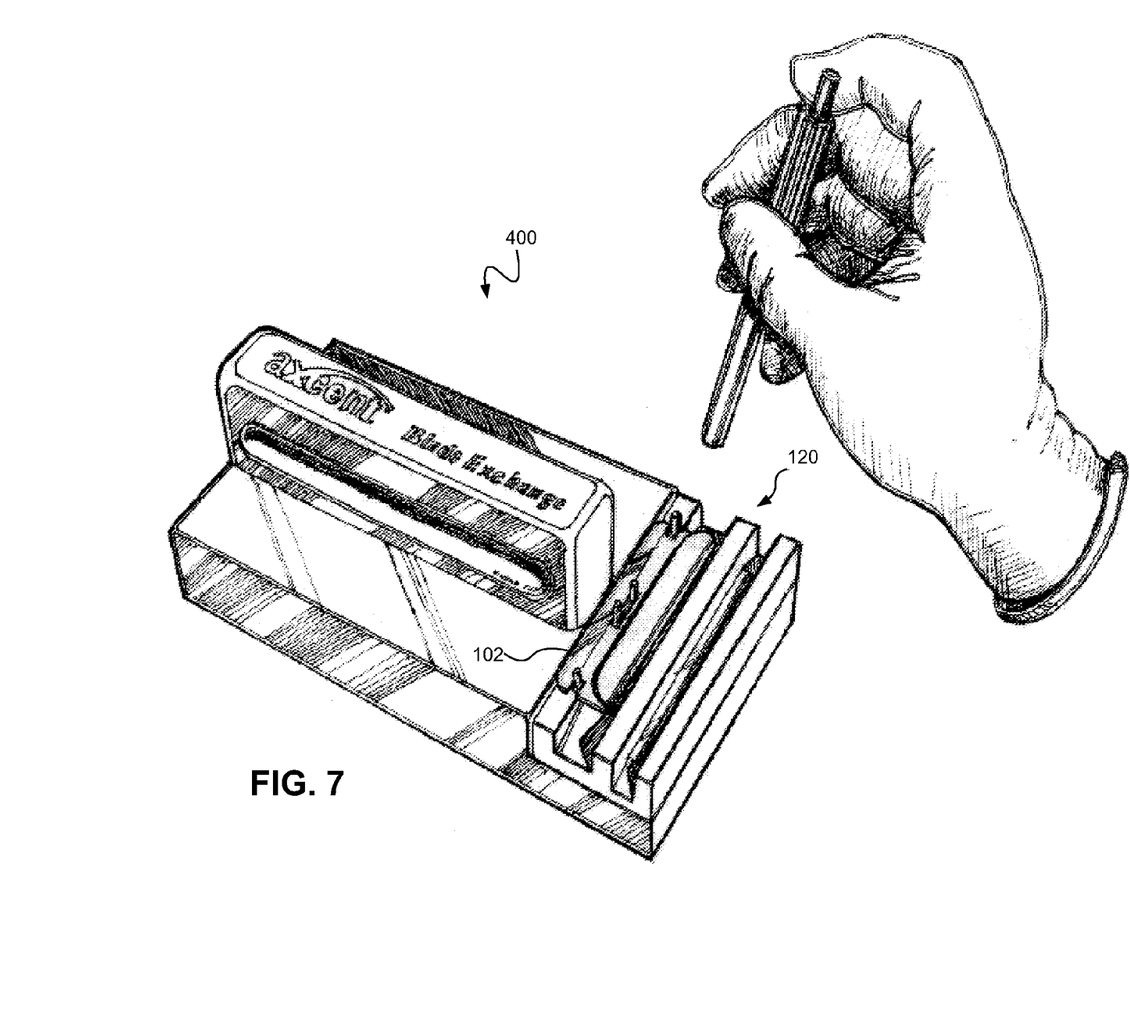
Figure 8:
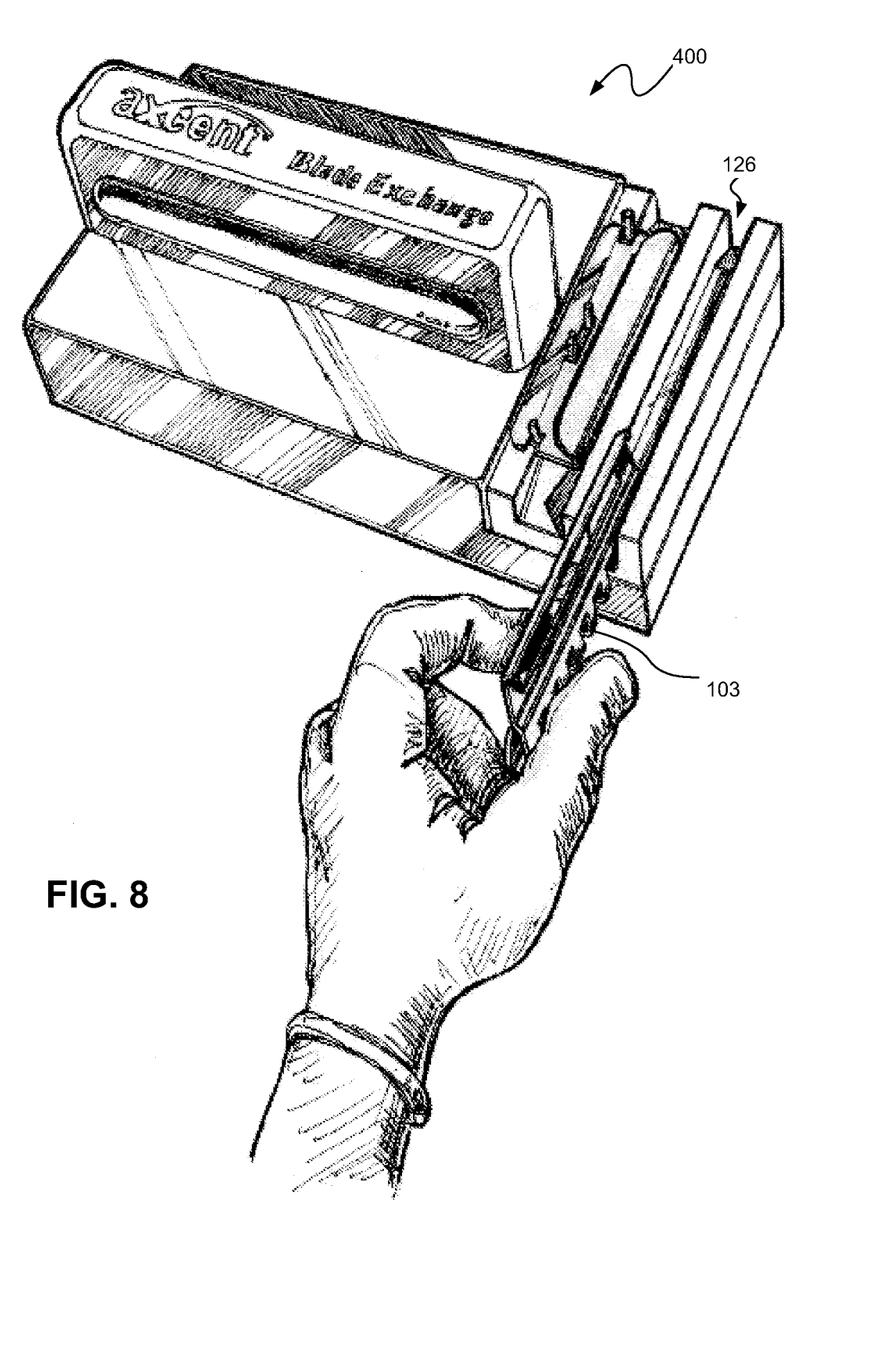
Figure 9:
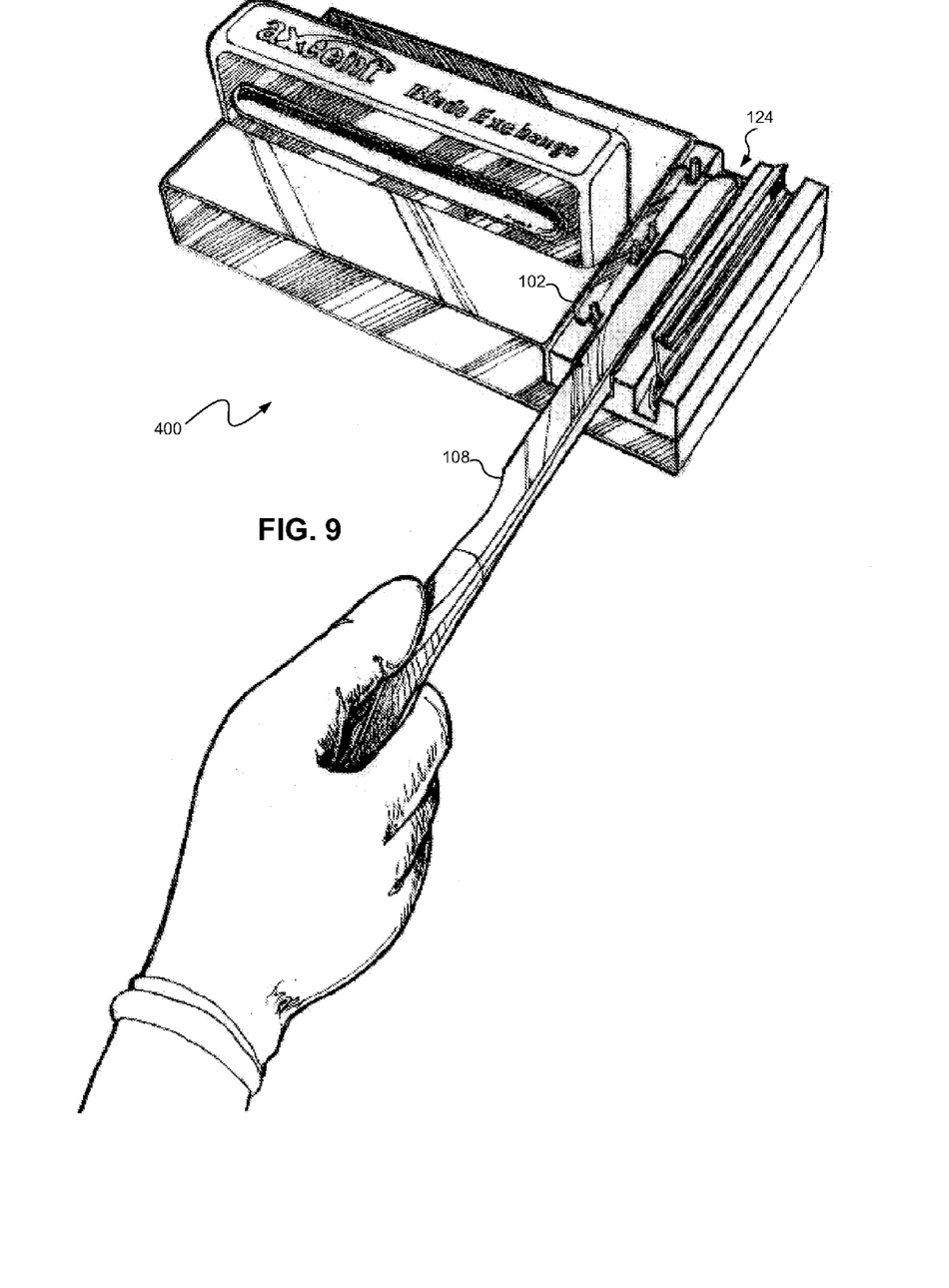
Figure 10:
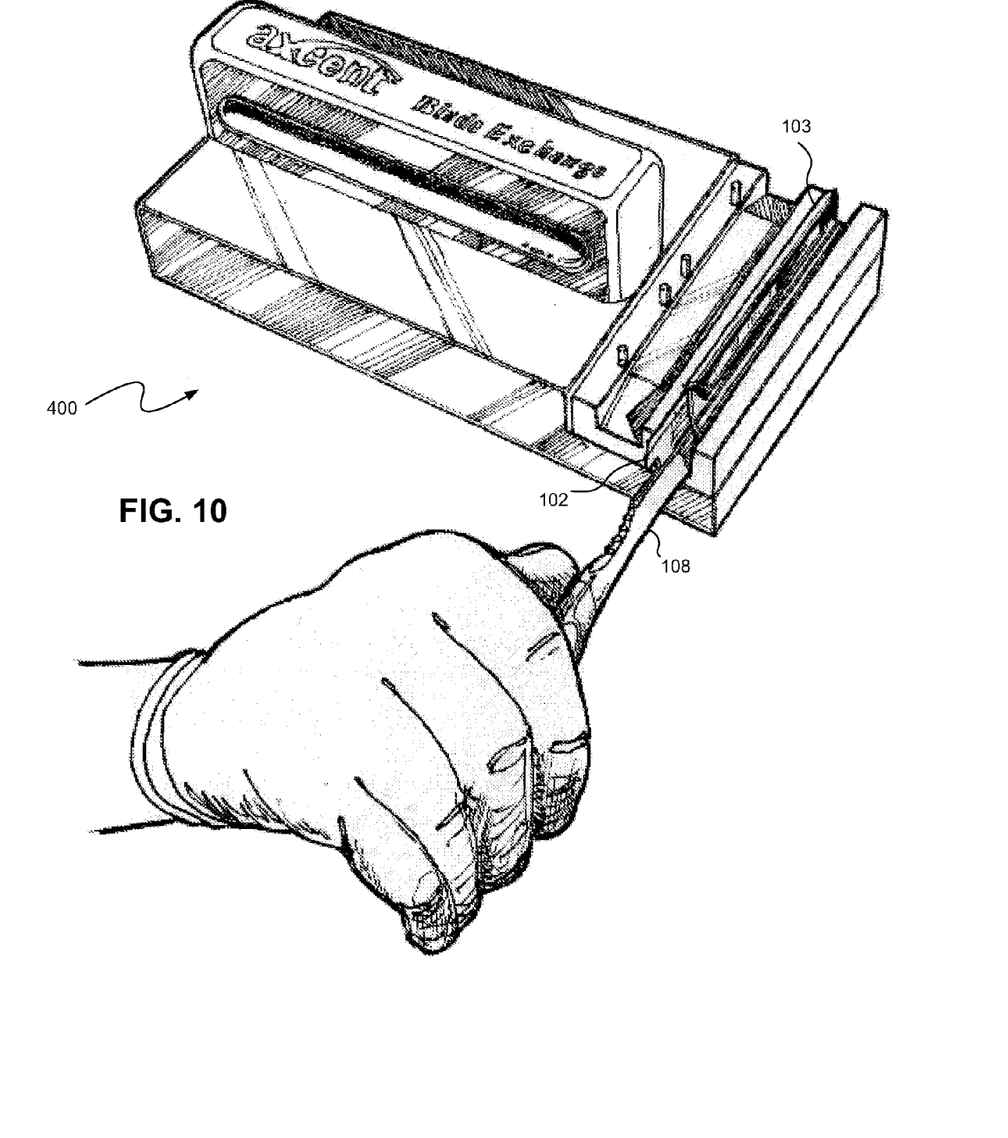
Figure 11:
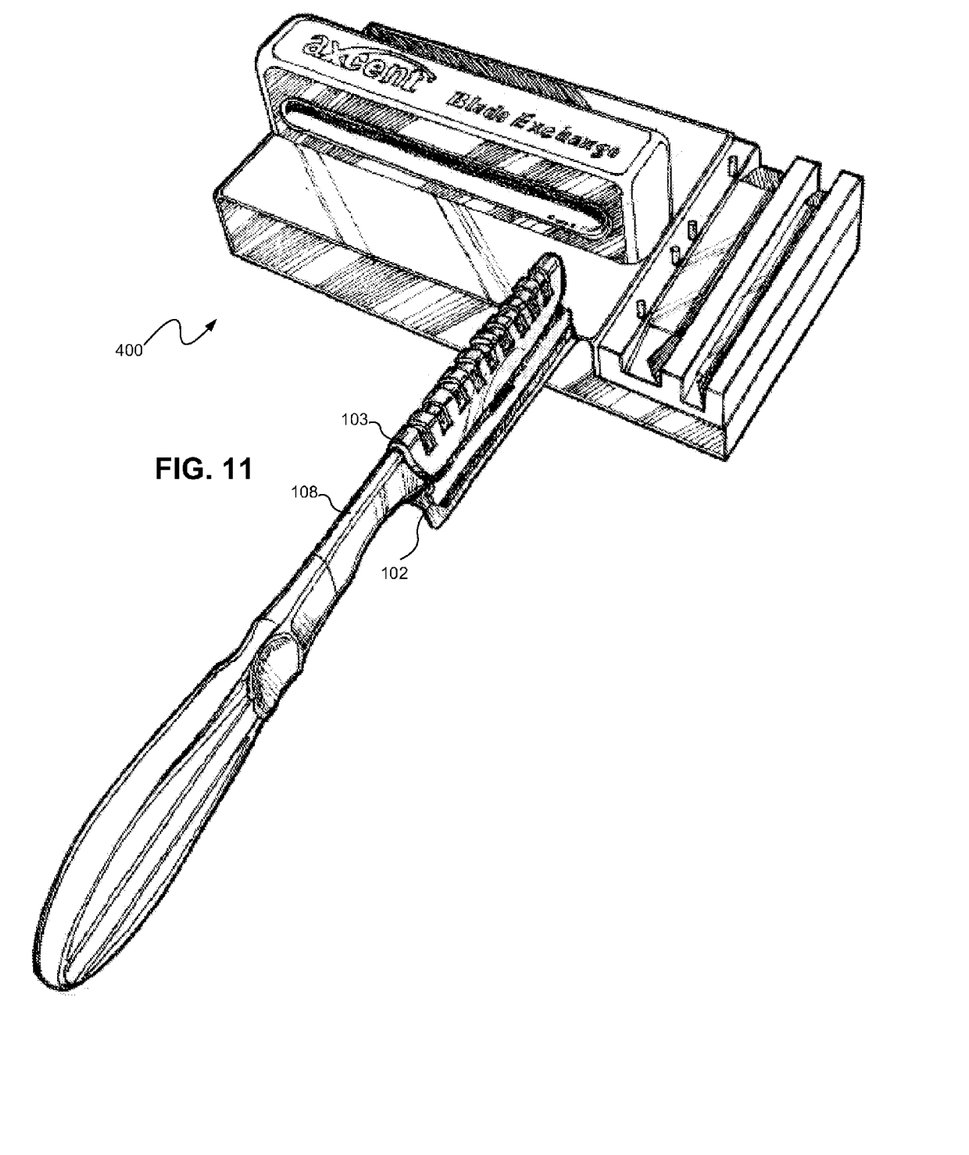

Referring to FIGS. 6-11, one embodiment of a blade installation method using a blade exchange system is shown and described in greater detail. The magnetic tool 500 may be used to couple a blade 102 (FIG. 6) and lift the blade onto the blade engaging portion 120 (FIG. 7). The hole 104 and notches 106 in the blade 102 are aligned with the pins 122 and the blade 102 is released such that the pins 122 extend through the hole 104 and notches 106. A blade guard 103 may be positioned within the blade guard receiving portion 126 (FIG. 8). The handle 108 may be slid into the handle receiving region 124 and onto one side of the blade 102 (FIG. 9). Although not shown, one hand of the user may be used to grasp the handle 230 of the blade exchange device 400 while the handle 108 of the instrument is slid to engage the blade 102. The handle 108 with the blade 102 secured at the blade securing end may then be lifted and positioned such that the blade 102 engages the blade guard 103 in the blade guard receiving region 126 (FIG. 10). The handle 108 and blade 102 are slid until the blade 102 fully engages the blade guard 103. The handle 108 with the blade 102 and blade guard 103 secured thereto may then be removed for use, for example, by lifting upward from the blade exchange device 400 (FIG. 11). To remove the blade after use, the above steps may be performed in reverse.

Accordingly, a blade exchange device, system and method may be used to remove and/or install blades on a medical or surgical instrument more effectively and safely.

Consistent with an embodiment, a blade exchange device is provided for removing or installing a blade secured in a handle. The blade exchange device includes a base portion and at least one blade engaging portion extending from the base portion. The blade engaging portion includes at least one locating protrusion corresponding to at least one hole or notch in a blade secured to a handle. The locating protrusion is configured to engage the hole or notch in the blade to hold the blade as the blade is engaged or disengaged from the handle. The blade engaging portion further includes a handle receiving region configured to receive the handle when the locating protrusion engages the hole or notch.

Consistent with another embodiment, a blade exchange system is provided for removing or installing a blade secured in a handle. The blade exchange system includes a blade exchange device including a base portion and at least one blade engaging portion extending from the base portion. The blade engaging portion including at least one locating protrusion corresponding to at least one hole or notch in a blade secured to a handle. The locating protrusion is configured to engage the hole or notch in the blade to hold the blade as the blade is engaged or disengaged from the handle. The blade engaging portion further includes a handle receiving region configured to receive the handle when the locating protrusion engages the hole or notch. The blade exchange system further includes a magnetic tool configured to magnetically attract a blade and to lift the blade to or from the blade engaging portion before the blade is installed or after the blade has been removed.

Consistent with a further embodiment, a system includes: a plurality of dermatome replacement blades configured to be engaged by a dermatome handle; a magnetic tool packaged with the blades and configured to magnetically attract the blades to facilitate removal or installation of the blades; and sterile packaging containing the blades and the magnetic tool.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A blade exchange device for removing or installing a blade secured in a handle, the blade exchange device comprising:
   a base portion;
   at least one blade engaging portion extending laterally from one end of the base portion, wherein a bottom surface of the blade engaging portion and the base portion is configured to contact a surface during use, the blade engaging portion including at least one locating protrusion corresponding to at least one hole or notch in a blade secured to a handle, the locating protrusion being configured to engage the hole or notch in the blade to hold the blade as the blade is engaged or disengaged from the handle, wherein the blade engaging portion is open to allow the blade to be transferred to or from the blade engaging portion before the blade is installed or after the blade has been removed, the blade engaging portion further including a handle receiving region configured to receive the handle when the locating protrusion engages the hole or notch, wherein the handle receiving region includes a channel extending below a top surface of the blade engaging portion from at least one side of the blade engaging portion; and
   a blade guard receiving region configured to receive and secure a blade guard and at least one blade guard engaging portion configured to engage the blade guard to prevent movement of the blade guard in at least one direction, wherein the blade guard receiving region includes a vertically-oriented well open on at least one side for receiving the handle with the blade when engaging the blade guard.

2. The blade exchange device of claim 1 wherein the handle receiving region includes at least one angled surface to allow alignment of the handle with the blade.

3. The blade exchange device of claim 1 wherein the handle receiving region extends from one side of the blade engaging portion to an opposite side of the blade engaging portion and includes first and second angled surfaces at each end.

4. The blade exchange device of claim 1 wherein the at least one blade guard engaging portion comprises a first blade engaging portion on a first end of the base portion and a second blade engaging portion on a second end of the base portion.

5. The blade exchange device of claim 1 further comprising:
   a handle portion extending from the base portion and configured to be grasped by a user.

6. The blade exchange device of claim 5 further comprising a shield located between the base portion and the blade engaging portion to shield a hand of a user from a blade.

7. The blade exchange device of claim 1 further comprising a shield located between the base portion and the blade engaging portion to shield a hand of a user from a blade.

8. The blade exchange device of claim 1 wherein the at least one locating protrusion includes a plurality of locating pins in a pattern corresponding to a pattern of holes and/or notches in a blade.

* * * * *